United States Patent [19]
Ahmed

[11] Patent Number: 5,981,470
[45] Date of Patent: Nov. 9, 1999

[54] UTERINE FIBROID TREATMENT

[75] Inventor: Asif Syed Ahmed, Birmingham, United Kingdom

[73] Assignee: The University of Birmingham, Birmingham, United Kingdom

[21] Appl. No.: 08/750,220

[22] PCT Filed: Jun. 6, 1994

[86] PCT No.: PCT/GB95/01301

§ 371 Date: Feb. 19, 1997

§ 102(e) Date: Feb. 19, 1997

[87] PCT Pub. No.: WO95/33454

PCT Pub. Date: Dec. 14, 1995

[30] Foreign Application Priority Data

Jun. 7, 1994 [GB] United Kingdom .................... 9411363
Oct. 6, 1994 [GB] United Kingdom .................... 9420212

[51] Int. Cl.$^6$ ..................................... A61K 38/00

[52] U.S. Cl. .............................. 514/2; 530/328; 530/329; 530/330; 530/332; 514/16; 514/17; 514/18; 514/19; 435/219; 548/535

[58] Field of Search ..................................... 514/16–19, 2; 530/328–331; 548/535

[56] References Cited

U.S. PATENT DOCUMENTS 5,407,955 4/1995 Bryant et al. ........................... 514/408

OTHER PUBLICATIONS

Nagasawa, K. et al., "Extracellular Matrix Deposition In Hypertensive Hearts. Antifibrotic Effects of Ramipril", *European Heart Journal*, vol. 16, Suppl. C, 1995 United Kingdom, pp. 33–37.

Campbell–Boswell, M. et al., "Effects of Angiotensin II and Vasopressin On Human Smooth Muscle Cells In Vitro", *Experimental And Molecular Pathology*, vol. 35, No. 2, 1981 USA, pp. 265–276.

Christiansen, JK, "The Facts About Fibroids, Presentation and Latest Management Options", *Postgraduate Medicine*, vol. 94, No. 3, 1993 USA, pp. 129–134.

Lumbers, E R et al., "Acute Effects of Captopril, An Angiotensin–Convertin Enzyme Inhibitor, On The Pregnant Ewe And Fetus", *American Journal of Physiology*, vol. 31, No. 5, 1992 USA, pp. R754–R760.

Primary Examiner—Cecilia J. Tsang
Assistant Examiner—David Lukton
Attorney, Agent, or Firm—Trexler, Bushnell, Giangiorgi & Blackstone, Ltd.

[57] ABSTRACT

The use of a) an angiotensin-converting enzyme (ACE) inhibitor such as Captopril or Enalapril, b) an angiotensin II-receptor antagonist such as Saralasin or Losartan, or c) a renin inhibitor, such as Remikiren or [N-(pyridyl-3-propionyl)-phenylalanyl-histidyl-(3S,4S) ACHPA-isoleucylamino]-2-methyl-2-dihydroxy-1,3-propane, for the manufacture of a medicament for the treatment of uterine fibroids is disclosed. The ACE inhibitor may be used concomitantly or sequentially with a gonadotropin-releasing hormone agonist such as Buserelin or Goserelin.

6 Claims, 5 Drawing Sheets

Effect of angiotensin II on myometrial cell growth

Effect of DuP753 on angiotensin II on myometrial cell growth

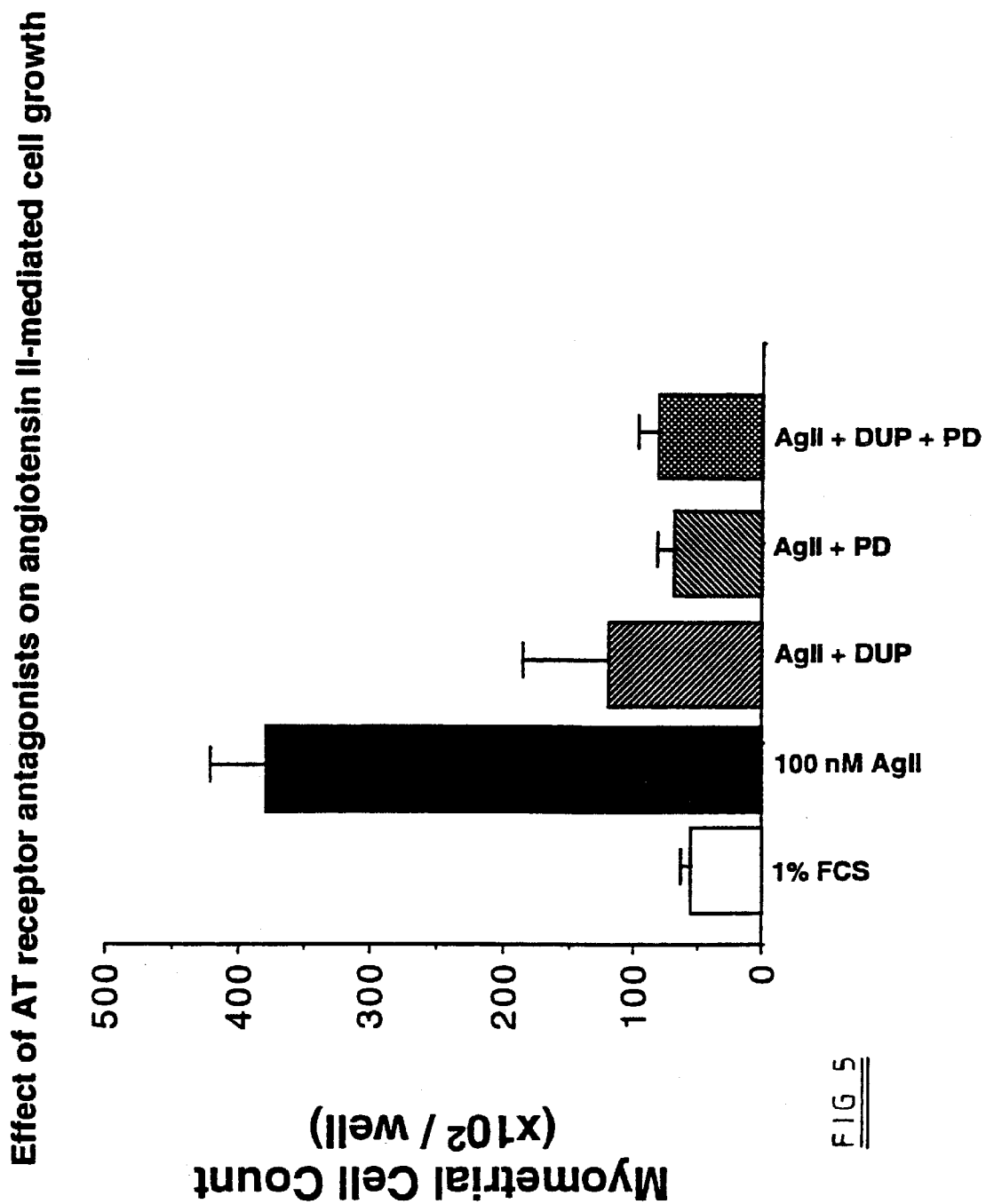

UTERINE FIBROID TREATMENT

BACKGROUND

This invention relates to uterine fibroid treatment.

Cellular proliferation and differentiation in uterine tissue is considered to be regulated by ovarian steroids as fibroids appear in the reproductive years and regress after the menopause. Uterine fibroids are most commonly treated by surgery, usually by full or partial hysterectomy, although removal of individual fibroids (myomectomy) is also undertaken at rather greater risk on women who have not completed child bearing. As far as medical treatment is concerned, agonist analogues of LHRH (luteinizing hormone-releasing hormone) such as Buserilin (GnRH analogue) have been employed to suppress oestrogen-progesterone as fibroids are ovarian steroid dependent. Such medical treatments, however, suffer from a variety of side effects such as predisposition to osteopetrosis and are not recommended for long term use.

SUMMARY

It is an object of the present invention to provide an alternative medical treatment for uterine fibroids which, it is believed, may have potential for use in situations where the above-mentioned medical treatments are inadvisable.

The present invention is based on the discoveries by the present inventor that angiotensin II (Type II) receptor ($AT_2$) is highly expressed in fibroid tissue compared to normal myometrium (see attached FIGS. 1(A) to 1(E)), and that angiotensin II stimulates myometrial cell proliferation (see FIGS. 3(A) and 3(B).

The present invention, in a first aspect, resides in the use of an angiotensin-converting enzyme (ACE) inhibitor for the manufacture of a medicament for the treatment of uterine fibroids.

The present invention, in a second aspect, resides in the use of an angiotensin II-receptor antagonist for the manufacture of a medicament for the treatment of uterine fibroids.

The present invention, in a third aspect, resides in the use of a renin inhibitor for the manufacture of a medicament for the treatment of uterine fibroids. In this connection, it is to be appreciated that, in the renin-angiotensin system (RAS), renin synthesized by the kidneys and secreted into the circulation cleaves the decapeptide angiotensin I from angiotensinogen. Angiotensin I is converted by ACE to the octapeptide angiotensin II which is the biologically active hormone. Accordingly, the use of a renin inhibitor will also have the effect of inhibiting angiotensin II.

In a fourth aspect, the present invention resides in the use of an angiotensin II receptor ($AT_1$ and/or $AT_2$) expression inhibitor (including an antisense oligonucleotide directed against the angiotensin II receptor ($AT_1$ and/or $AT_2$) expression gene) in the manufacture of a medicament for the treatment of fibroids.

With regard to said first aspect of the present invention, namely the use of an ACE inhibitor to suppress angiotensin II expression, it is considered that any ACE inhibitor can potentially be used, including those which are known and which have been used or proposed to be used for ACE inhibition in the treatment of hypertension and congestive heart failure.

For example, ACE inhibitors such as Captopril (very soluble in water) and Enalapril (CAS 75847-73-3) (sparingly soluble in water) have relatively few side effects and are very effective in the treatment of hypertension.

Other ACE inhibitors which may be suitable are:

Benazepril,
Ramipril,
Lisinopril,
Imidapril 6366A (CAS 89371-44-8) (Arzneim. Forsch./Drug Res., September 1992, 42(9), pages 1109–14),
N-[8-amino-1(S)-carboxyoctyl]-L-alanyl-L-proline (AB-47, CAS 120008-53-9)
Pimobendan (CAS 118428-36-7) (Arzneim. Forsch./Drug Res. 43(1) No. 2a, 1993, pages 233–235), and antisense oligonucleotides directed against the ACE gene or against genes for other enzymes in the renin-angiotensin system.

With regard to angiotensin II receptor antagonists, it is considered that suitable antagonists can be found amongst the following:

Saralasin,
Losartan (DuP753) (CAS 124750-99-8),
PD 123177,
CGP 42112A,
BIBS 39,
BIBS 222,
Sar-Ile-Ang II,
Sar-Thr-Ang II,
Sar-Ala-Ang II,
Sar-Val-Ala-Ang II,
Sar-O-Me-Tyr-Ang II
(see Arzneim. Forsch./Drug Res., 43(1) No. 2a (1993), pages 214–246).

As far as renin inhibitors are concerned, it is considered that suitable renin inhibitors may be:

Remikiren ($R_o$42-5892, CAS 126371-83-3)
[N-(pyridyl-3-propionyl)-phenylalanyl-histidyl-(3S,4S) ACHPA-isoleucylamino]-2-methyl-2-dihydroxy-1,3-propane (Arzneim. Forsch./Drug Res., Feb 1993 43(2A), pages 255–259).

Other renin inhibitors may be C1-992 (J. Pharmacol. Exp. Ther., 268:372–9, 1994); non-peptide renin inhibitors containing 2-(((3-phenylpropyl)phosphoryl)oxy)alkanoic acid moieties as $P_2$–$P_3$ replacements (J. Med. Chem. 37:486–97, 1994) and antisense oligonucleotides directed against the renin-expression gene.

The ACE inhibitor, angiotensin II-receptor antagonist (e.g. Saralasin, Losartan or PD 123177) or an angiotensin II receptor ($AT_1$ and/or $AT_2$) expression inhibitor (including an antisense oligonucleotide directed against the angiotensin II receptor ($AT_1$ and/or $AT_2$) expression gene) may be used concomitantly or sequentially with a gonadotropin-releasing hormone agonist (GnRH—A) such as Buserelin or Goserelin in the treatment of uterine fibroids to reduce the size thereof.

Accordingly, the present invention further resides in the use of an angiotensin-converting enzyme (ACE) inhibitor or an angiotensin II-receptor antagonist for the manufacture of a medicament for the treatment of uterine fibroids, concomitantly or sequentially with gonadotropin-releasing hormone agonist (GnRH—A) such as Buserelin or Goserelin.

The present invention also resides in the concomitant or sequential use of (a) an ACE inhibitor (e.g. Ramipril, Lisinopril or Enalapril), or an angiotensin II-receptor antagonist (e.g. Saralasin, Losartan or PD 123177) with (b) a gonadotropin-releasing hormone agonist (GnRH—A) such as Buserelin or Goserelin in a method of the treating uterine fibroids.

Such use may comprise administration of a medicament comprising a mixture of (a) and (b), or administration of a medicament containing (a) and a medicament containing (b) either concomitantly or sequentially. Medicament (a) may be administered before medicament (b) or vice versa.

BRIEF DESCRIPTION OF THE DRAWINGS

In FIGS. 1A–1E, dark regions indicate high densities of labeled receptors.

In FIGS. 2A–2J, dark regions indicate high densities of labeled receptors.

FIG. 5: Effect of an AT receptor antagonist on angiotensin II-mediated cell growth.

DETAILED DESCRIPTION OF THE INVENTION

Figure 1:
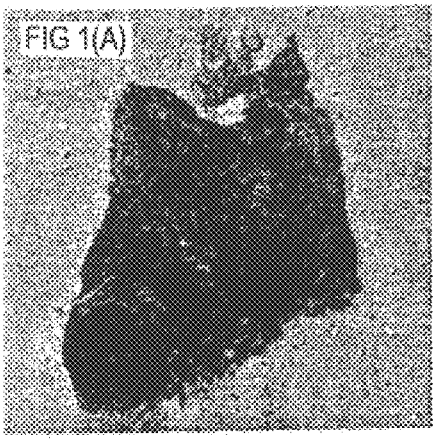
FIGS. 1A–1E: Autoradiograms of the distribution of [$^{125}$I]-angiotensin II binding to adjacent sections (20 μm) of the human non-pregnant myometrium containing a fibroid. (A) Total binding; (B) binding in the presence of the $AT_1$ receptor selective ligand DuP753 (1.0 μM); (C) binding in the presence of the $AT_2$ receptor selective ligand PD123177 (1.0 μM); (D) binding in the presence of DuP753 (1.0 μM) plus PD 123177 (1.0 μM); (E) binding in the presence of unlabeled angiotensin II (0.1 nM).
Figure 1:
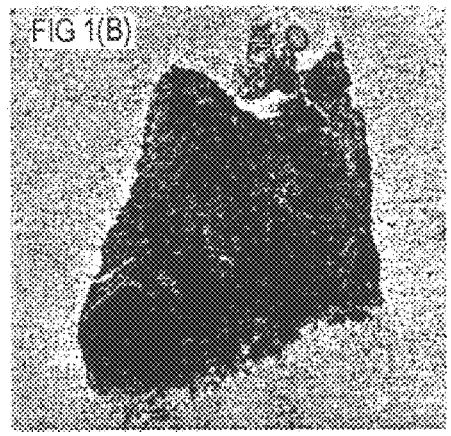
Figure 1:
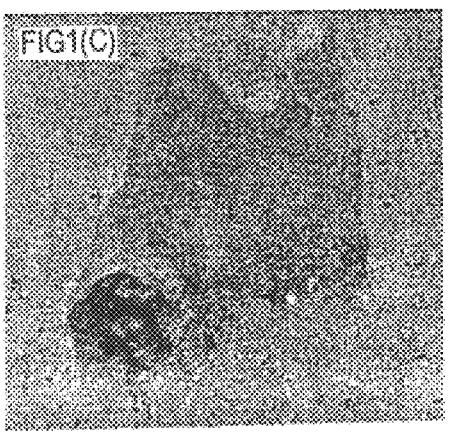
Figure 1:
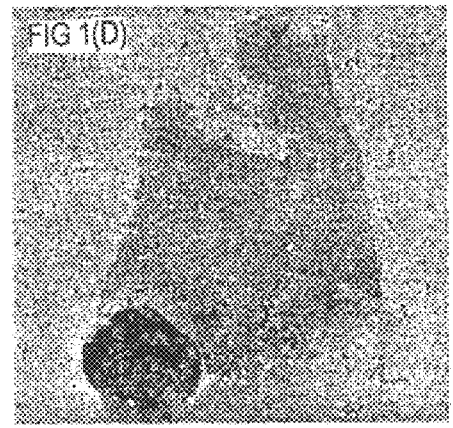
Figure 1:
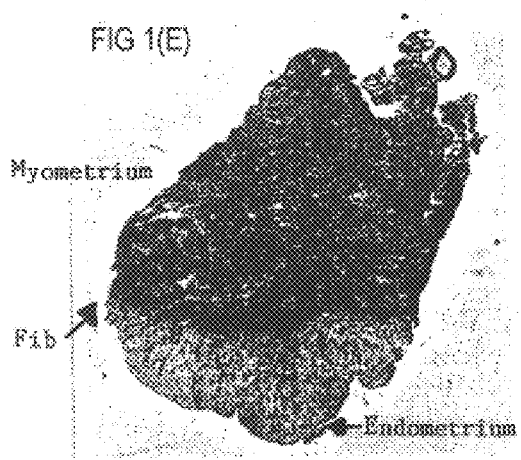
Figure 1:
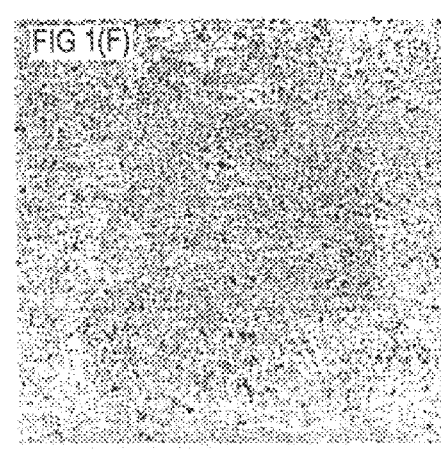

The present invention will now be described in further detail.

Materials and Methods

Materials

[$^{125}$I]Angiotensin II (2200 Ci/mmol) was purchased from Amersham International Plc (Amersham, Berks U.K.). Angiotensin II, saralasin and other reagents unless otherwise specified were purchased from Sigma Chemical Co. (Poole, Dorset, U.K.). Basic fibroblast growth factor (bFGF) was purchased from RD Systems (Minneapolis, U.S.A). Losartan (DuP753; (2-n-butyl-4-chloro-5-hydroxymethyl-1-[2-(1H-tetrazol-5-yl)biphenyl-4-yl)methyl]imidazole) and PD123177 (1-(4-amino-3-methylphenyl)-methyl-5-diphenyl-acetyl-4,5,6,7-tetrahydro-1H-imidazo[4,5-C] pyridine-6-carboxylic acid) were from DuPont Merck Pharmaceuticals and kindly provided by Dr. N. M. Barnes, University of Birmingham. Components for the culture medium were obtained from Flow Laboratories (High Wycombe, Berks., U.K.).

Source of Tissue

Myometrium was collected from women undergoing total abdominal hysterectomy. Patients selected had no apparent endocrinological problems and no local organic pathologies. All tissues were obtained from 20–48 year old women with a history of regular menstrual cycles. None of the patients had taken any hormonal medication for at least 3 months before the surgery. The tissue was rinsed in sterile saline and rapidly frozen over dry-ice, wrapped in Parafilm to prevent dehydration and stored at −70° C. until they were sectioned for receptor autoradiographic studies.

Preparation of Tissue Sections

Frozen myometrium and fibroid tissues were surrounded in embedding medium (OCT compound, Miles Scientific) before 20 μm sections were cut using a cryostat (−15 to −1 9° C.) and thaw mounted onto gelatin-coated glass slides for receptor autoradiographic studies. Sections were stored (less than 2 week) desiccated at −80° C. until used.

Myometrial Cell Preparation

Tissue samples were placed into sterile calcium and magnesium-free HBSS containing penicillin (100 U/ml) and streptomycin (100 μg/ml) for transfer to the laboratory. Myometrial cells were isolated by collagenase digestion. Briefly, myometrium was finely chopped and incubated in HBSS containing 1 mg/ml collagenase IA, 20 mM Hepes, 100 U/L penicillin, 100 μg/ml streptomycin and 5 μg/ml fungizone at 37° C. until the cells were dispersed. Myometrial cells were obtained by centrifugation for 15 minutes at 400 g over 60% Percoll and the cells washed with HBSS. Myometrial cells were characterised by their ability to respond to oxytocin and staining for actin.

[$^{125}$I]Angiotensin II Autoradiography

Slide mounted human myometrial/fibroid sections were removed from storage and allowed approximately 30 min to equilibrate to room temperature. To reduce endogenous levels of angiotensin II in the tissue, the sections were preincubated for 60 min in incubation buffer (mM; sodium chloride, 150; sodium dihydrogen phosphate, 50; magnesium chloride, 10; ethyleneglycol-bis-(β-amino-ethyl ether)-N,N'-tetra-acetic acid, 5 and 0.4% w/v bovine serum albumin, pH 7.4) at 25° C. The slides were then incubated in incubation buffer which contained 0.1 nM [$^{125}$I ]angiotensin II in the absence (total binding) or presence of competing compound (either 1.0 μm unlabelled angiotensin II, 1.0 μM DuP753, 1.0 μm PD123177 or 1.0 μm DuP753 plus 1.0 μm PD123177) for 60 min at 25° C. Immediately following incubation, the tissue sections were washed in ice-cold incubation buffer for 2 min and dipped (1 s) in ice-cold distilled water to remove buffer salts. The sections were rapidly dried in a stream of cold dry air and exposed to Hyperfilm-[$^3$H] (Amersham International) in X-ray cassettes together with [$^{125}$I] standards (Amersham International) for 10 days. Autoradiographic films were developed in Kodak LX 24 developer (5 min) and Kodak Unifix (5 min) and were quantitated by reference to [$^{125}$I] standards (fmol/mg tissue; Amersham) using image analysis.

Cell Culture and Cell Proliferation Studies

Cells were maintained in 175 cm$^2$ flasks in Dulbecco's modified Eagle's medium (DMEM) containing 10% (v/v) fetal calf serum (FCS), 1% L-glutamine, 20 mM Hepes and 1% antibiotic-antimycotic mixture (10,000 U penicillin, 10 μg streptomycin, and 25 μg ml$^{-1}$ fungizone) at 37° C. in a humidified atmosphere of air/CO$_2$(19:1) until 95% confluent. Thereafter, the cells were trypsinised, washed and re-plated at a density of 10×10$^3$ cells per well in 24-well plates in 1 ml of DMEM with 10% FCS for the proliferation studies. After 24 hrs, the medium was removed and replaced with serum-free DMEM. After a further 24 hrs, the experiments were initiated on quiescent monolayers of myometrial cells. To the serum-starved myometrial cells was added either angiotensin II (0.1 μm or 1.0 μm) in the presence or absence of 1% FCS or bFGF (20 ng/ml) or FCS (1%) alone or DuP753 with or without angiotensin II (0.1 μM) and cell growth measured at day 4 and day 6 by counting cell numbers in a Coulter counter as described below. The corresponding medium was replaced every 24 hrs with fresh medium.

Calibration of the Coulter Counter

Calibration of the Coulter counter was achieved by counting the myometrium cell suspension at reduced aperture size ranging from 0 to 32. A calibration curve was constructed from the cell counts on the function of the aperture size, and the aperture size corresponding to the middle point of the plateau part of the calibration curve was used for the cell counting. The aperture size used for myometrium cell counting was 16.

Counting of the Myometrium Cells

At defined time-points, the growth media was removed and the cells were washed with 1 ml of isotonic saline (0.9% sodium chloride), followed by the addition of 1 ml of 10 mM HEPES buffer containing 1.5 mM magnesium chloride, and 2 drops of Zap-oglobin (Coulter Electronics Ltd., Luton, Beds., UK) containing 2.5% acetic acid to each well. The 24-well plate was allowed to incubate at 37° C. for 10 min. After which, the suspended cells were pipetted up and down to disperse the cell clusters. The cell suspension was then added to 9 ml of counting solution containing 0.9% sodium chloride and 0.5% formalin in a Coulter counter container. Each well was washed three times with the counting solution from the same container and effluent collected in the same container. The number of cells in each well was counted at the aperture size of 16 on the Coulter counter (Coulter Electronics Ltd., Luton, Beds U.K.). Three readings were taken for each well and a mean value of the three readings obtained. The mean (±SD) value of cell counts from the triplicate wells was calculated.

Results and Discussion

Expression of Angiotensin II Receptor Subtypes

Figure 2:
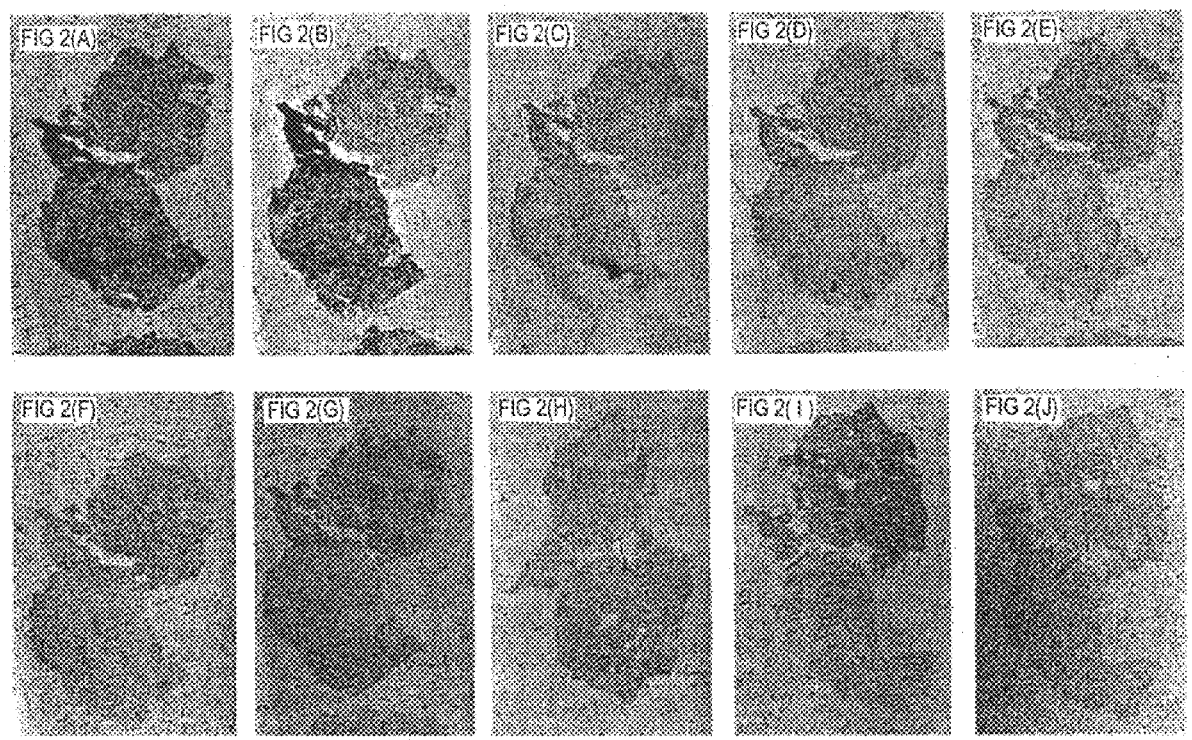
FIGS. 2A–2J: Autoradiograms of the distribution of $^{125}$I-angiotensin II binding to adjacent sections of the human non-pregnant myometrium and fibroid. (A) Total binding; (B) binding in the presence of the $AT_1$ receptor selective ligand DuP753 (1.0 μM); (C) binding in the presence of the $AT_2$ receptor selective ligand PD123177 (1.0 μM); (D) binding in the presence of DuP753 (1.0 μM) plus PD123177 (1.0 μM); (E) binding in the presence of unlabeled angiotensin II (AngII, 0.1 nM); (F) binding in the presence of unlabeled angiotensin I (AngI, 0.1 nM); (G) binding in the presence of unlabeled angiotensin III (AngIII, 0.1 nM); (H) binding in the presence of unlabeled Sar-Thr-angiotensin II (0.1 nM); (I) binding in the presence of unlabeled Amino-Phe-angiotensin II (0.1 nM); (J) binding in the presence of unlabeled Sar-Ala-angiotensin II (0.1 nM).

With the development of non-peptide angiotensin II receptor (AT) antagonists, attention has focused on the AT receptor as a target to pharmacologically manipulate the renin-angiotensin system. Using quantitative receptor autoradiography, we have pharmacologically characterised the presence of $AT_2$ receptors on non-pregnant myometrium and fibroids (FIG. 1). Dark regions indicate high density of labelled receptors. It is clear from the FIG. 1 that the fibroid region contains a higher density of angiotensin II receptors than normal myometrium. FIG. 1(A) to 1(E) are autoradiograms of the distribution of [$^{125}$I]angiotensin II binding to adjacent sections (20 μm) of the human non-pregnant myometrium containing a fibroid. In FIG. 1(A), total binding of such labelled angiotensin II is illustrated. FIG. 1(B) shows binding in the presence of the $AT_1$ receptor selective ligand DuP753 (1.0 μm). FIG. 1(C) shows binding in the presence of the $AT_2$ receptor selective ligand PD123177 (1.0 μm). FIG. 1(D) shows binding in the presence of DuP753 (1.0 μM) plus PD123177 (1.0 μM). FIG. 1(E) shows binding in the presence of unlabelled angiotensin II (0.1 nM). Dark regions indicate high densities of labelled receptors. The difference in density between FIGS. 1(A) and 1(B) represents $AT_1$ receptor specific binding. This receptor subtype is weakly expressed in myometrium. The difference in density between FIGS. 1(A) and 1(C) represents $AT_2$ receptor specific binding. The fibroid region in FIG. 1(C) shows a lower AT receptor expression than the same region in FIG. 1(B), thus indicating that the fibroid has predominantly $AT_2$ type receptors. The fibroid had a higher density of angiotensin II receptors than normal myometrium. The difference between FIG. 1(A) and 1(D) represents specific $AT_1$ plus $AT_2$ receptor-density, and the difference between FIG. 1(D) and 1(E) represents a newly discovered, non-$AT_1$/non-$AT_2$ angiotensin II recognition site. The intensity of expression of such non-$AT_1$/non-$AT_2$ angiotensin II recognition site in the fibroid tissue only disappears in the presence of cold angiotensin II (1 μM), thus indicating that this is an additional high affinity angiotensin II recognition site. This newly discovered site is pharmacologically distinct from known AT receptor subtypes, and Sar-Thr-angiotensin II and Sar-Ala-angiotensin II can selectively displace [$^{125}$I]angiotensin II from this site (FIG. 2).

Angiotensin II-induced Myometrial Cell Proliferation

Figure 3A:
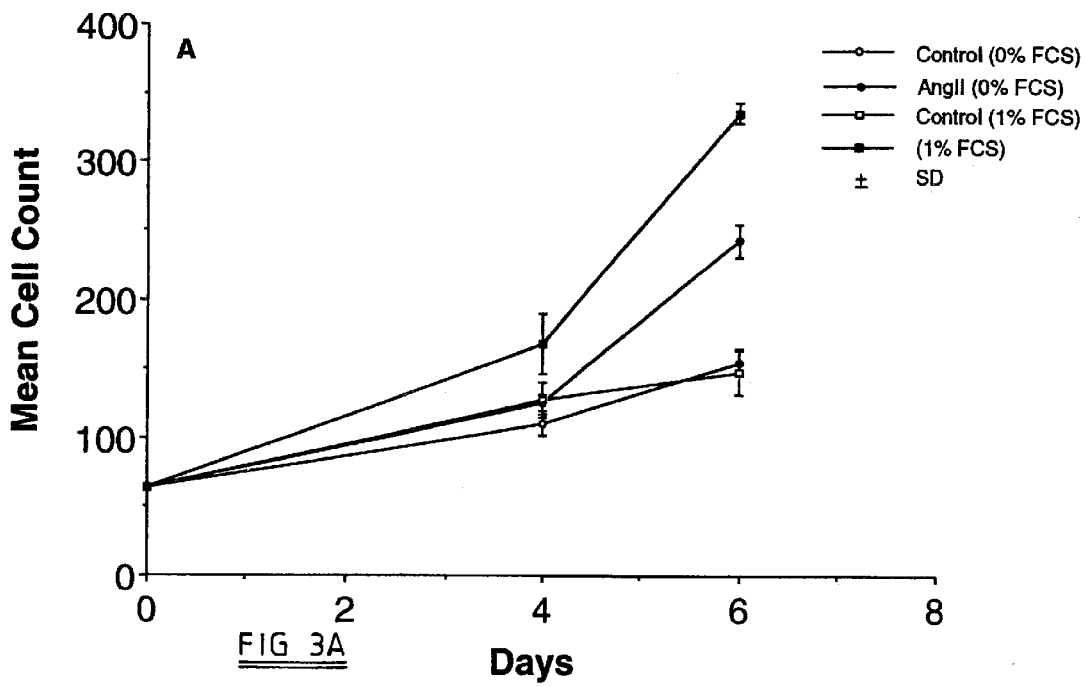
FIGS. 3A–3B: Effect of angiotensin II and an AT, receptor ligand on angiotensin II-induced myometrial cell proliferation. (A) Effect of angiotensin II on myometrial cell proliferation; (B) effect of $AT_1$ receptor ligand DuP753 on angiotensin II-induced myometrial cell proliferation.
Figure 3B:
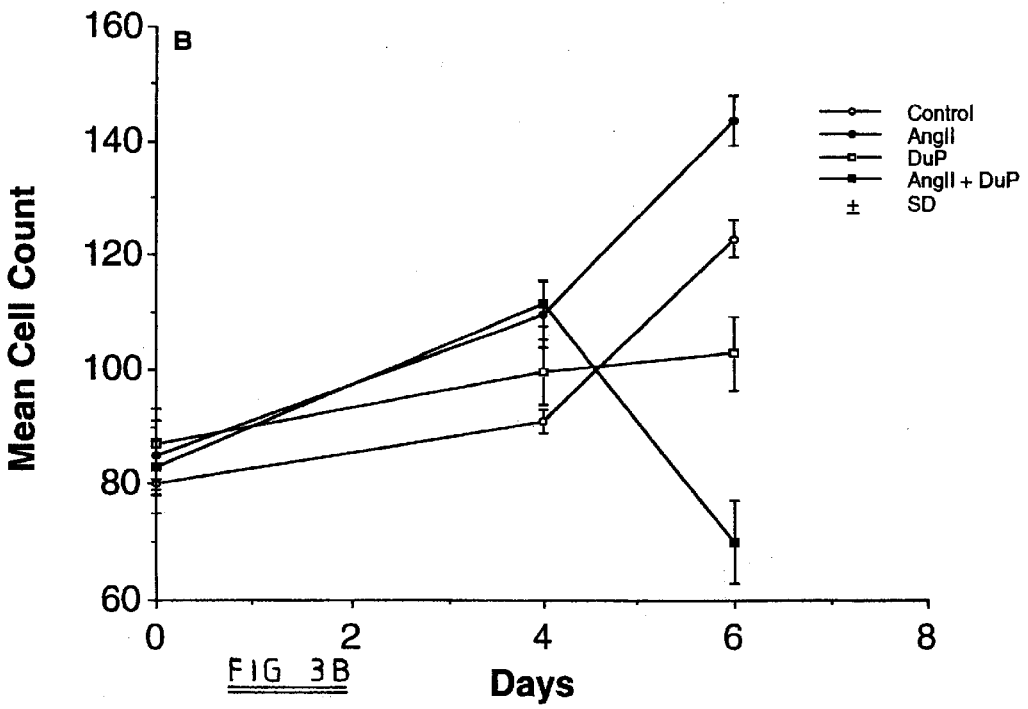

The results of growth experiments are given in attached FIG. 3(A) and 3(B) which are graphs plotting mean cell count against time in days. It will be seen from FIG. 3(A) that the presence of angiotensin II (0.1 μM) in culture medium has a significant effect on myometrial cell growth and that after six days in culture there is approximately a 100% increase in myometrial cell proliferation compared to cells in culture medium devoid of angiotensin II. It is also interesting to note that the angiotensin II-induced response is comparable to that induced by a classic growth factor such as bFGF (Table 1).

TABLE 1

| | Days | | |
|---|---|---|---|
| | 0 day (+/−SD) | 4 days (+/−SD) | 6 days (+/−SD) |
| Control (1% FCS) | 65.83 +/− 1.52 | 127.00 +/− 12.53 | 146.33 +/− 16.22 |
| Ag II (0.1 μM in 1% FCS) | 64.33 +/− 2.73 | 167.33 +/− 21.55 | 333.67 +/− 7.51 |
| bFGF (20 ng/ml in 1% FCS) | 63.90 +/− 1.88 | 167.33 +/− 25.11 | 307.33 +/− 49.69 |

In addition, angiotensin II receptor antagonists blocked the effect of angiotensin II on cell proliferation. It can be seen in FIG. 3(B) as an example that DuP753 inhibits the effects of angiotensin II on cell proliferation. Preliminary data also shows that PD177123 also inhibits angiotensin II-mediated cell growth. Consequently, it is reasonable to infer that reduction of the level of angiotensin II or blocking of the high affinity angiotensin II binding sites in the fibroid will lead to a reduction in, or inhibition of, fibroid growth.

Patient Treatment Regimes

The invention proposes to treat patients in one of the following ways:

(1) By oral administration of the drug and this may be the preferred method of treatment.
(2) intravaginal administration using a vaginal ring
(3) adding drug via a intrauterine device
(4) directly at the site of the tumour using an ultrasound directed local injection into the fibroid (as some of these compounds are water soluble, they could be placed in an oil-based solution and then injected so as to give slow release of the active drug).
(5) as a pellet inserted directly at the site of the tumour using the long-acting near-zero order releasing system with the aid of laproscopy.

As discussed above, FIGS. 1A–1E are different autoradiograms of the distribution of [$^{125}$I]-angiotensin II binding to adjacent sections (20 μm) of the human non-pregnant myometrium containing a fibroid. The difference in density between (A) and (B) represents $AT_1$ receptor specific binding (this receptor subtype is not detected in myometrium); difference in density between (A) and (C) represents $AT_2$ receptor specific binding; difference between (A) and (D) represents specific $AT_1$ plus $AT_2$ receptor density and the difference between (D) and (E) represents the newly discovered, non-$AT_1$/non $AT_2$ angiotensin II recognition site. Note the intensity of expression of such non-$AT_1$/non-$AT_2$ angiotensin II recognition site in the fibroid tissue which only disappears in the presence of cold angiotensin II suggesting that the fibroid expresses high levels of the binding site.

As discussed above, FIGS. 2A–2J are different autoradiograms of the distribution of [$^{125}$I]angiotensin II binding to adjacent sections (20 μm) of the human non-pregnant myometrium (Myo) and fibroid (Fib).

As discussed above, FIG. 3(A) illutrates the effect of angiotensin II on myometrial cell proliferation. Myometrium cells were maintained in Dulbecco's modified Eagle's medium (MD) with 10% (v/v) FCS, containing 1% L-glutamine, 20 mM HEPES and 1% antibiotic-antimycotic mixture (10,000 U penicillin, 10 mg streptomycin) at 37° C. in a humidified atmosphere of air/$CO_2$ (19:1) until 95% confluent. For the proliferation studies, the cells were plated at a density of $10\times10^3$ cells per well in 24 well plates in 1 ml of DMEM with 10% FCS. After 24 hrs the medium was removed and replaced with serum-free DMEM. After a further 24 hrs, the experiment was initiated on quiescent monolayers of myometrial cells. To each of the wells in triplicate was added 1 ml of angiotensin II (0.1 μM) or DMEM alone, in the presence or absence of 1% FCS. The cell growth was measured at day 4 and day 6 by counting cell numbers in a Coulter Counter. Each point represents the mean ± sem of triplicate determinations from a single experiment, typical of three others.

As discussed above, FIG. 3(B) illustrates the effect of $AT_1$ receptor ligand (DuP753) on angiotensin II-induced myometrial cell proliferation.

Myometrium cells were maintained in Dulbecco's modified Eagle's medium (MD) with 10% (v/v) FCS, containing 1% L-glutamine, 20 mM HEPES and 1% antibiotic-antimycotic mixture (10,000 U penicillin, 10 mg streptomycin) at 37° C. in a humidified atmosphere of air/$CO_2$ (19:1) until 95% confluent. For the proliferation studies, the cells were plated at a density of $10\times10^3$ cells per well in 24 well plates in 1 ml of DMEM with 10% FCS. After 24 hrs the medium was removed and replaced with serum-free DMEM. After a further 24 hrs, the experiment was initiated on quiescent monolayers of myometrial cells. To each of the wells, in triplicate, was added 1 ml of 1% FCS as control or angiotensin II (0.1 μM), or DuP753 (1 μM) or DuP753 plus angiotensin II (0.1 μM) in the presence of 1% FCS. The cell growth was measured at day 4 and day 6 by counting cell numbers in a Coulter Counter. Each point represents the mean ± sem of triplicate determinations from a single experiment, typical of three others.

A further series of experiments were conducted as described below:

Immunocytochemistry

Serial 3 μm sections of formalin-fixed, paraffin-embedded tissue were used for immunohistochemistry. Sections were de-paraffinized by incubation for 5 min with Histoclear and hydrated through methanol to water. Endogenous peroxidase activity was quenched by 0.3% (v/v) hydrogen peroxide in methanol for 10 minutes. The primary antibodies were rabbit polyclonal antibodies raised against the human renin, angiotensin converting enzyme, ANG1, ANG II and $AT_1$ receptor. Non-immune goat serum (10% in 0.01 mol/l PBS, pH 7.2) was used as a dilution of the primary antibody to reduce non-specific binding. Amplification of the primary antibody reaction was achieved using a goat anti-rabbit secondary antibody (diluted 1:200 in 0.01 mol/l PBS, pH 7.2) for 30 min followed by a complex of streptavidin (Dako Ltd, Bucks, UK) and biotinylated peroxidase (Dako Ltd, Bucks, UK). Finally, the binding was visualised by the addition of 0.5 mg/ml diaminobenzidine (Sigma Chemical Co. Ltd, Poole, Dorset, UK) and 0.01% hydrogen peroxide in 0.01 mmol/l PBS to the antigen-antibody complex. Between each step the sections were washed in 3×200 ml of 0.1% (v/v) polyoxylene-10-oleoyl-ether in 0.01 mmol/l PBS, pH 7.2, over a period of 15 min. All incubations of antisera were carried out at room temperature in a wet chamber mounted on a rocking tray which ensures a movement of antiserum over the whole section. The sections were counterstained with Mayers Haematoxylin, dehydrated and mounted.

Results

Using the immunocytochemistry described above, the primary antibodies raised against renin, angiotensin converting enzyme, angiotensin I and angiotensin II were used to show that the components of the renin-angiotensin system (RAS) are expressed in myometrium and fibroids. This suggests that there is local RAS within the tissue itself, further supporting the functional studies. In addition, immunoreactive $AT_1$ receptor protein was localised in myometrial smooth muscle cells and around the blood vessels, indicating that myometrium and fibroid tissues contain $AT_1$ receptors in addition to $AT_2$ receptors which were clearly identified using autoradiography results. Evidence also indicates that there is intense vascularization around the uterine fibroid and also within the fibroids as QBN10 (a marker of endothelial cells) intense endothelial cell staining in immunohistochemical sections.

Cell Culture and Measurement of [$^3$H]-thymidine Incorporation

Myometrial cells prepared as described previously were resuspended in culture medium containing DMEM supplemented with 10% (v/v) FCS, 10 mM L-glutamine, 20 mM hepes, 100 U/mi penicillin and 100/μg/ml streptomycin in 24 well plates at a density of approximately $250\times10^3$ cells per well and maintained at 37° C. in a humidified atmosphere of air/$CO_2$ (19:1).

DNA synthesis was assayed by measuring [$^3$H]-thymidine incorporation into DNA. Subconfluent myometrial cells were made quiescent by incubation with serum-free medium for 48 h, the medium being replaced with serum-free medium containing 0.2% (w/v) bovine serum albumin (BSA) and [$^3$H]-thymidine (0.2 μCi/well). The cells were further incubated for 48 h in the presence of angiotensin-converting enzyme (ACE) inhibitor (0.1 and 1.0 mM Captopril, hatched and solid columns respectively) or angiotensin II (100 nM AgII, crossed column). The medium was then removed and the cells incubated with 10% cold trichloroacetic acid TCA) at 4° C. for 15 min. TCA-precipitated material was redissolved in 0.2 M NaOH and the radioactivity determined by liquid scintillation counting in a β-scintillation analyser. Positive and negative controls for proliferation were established by incubating cells with 10% fetal calf serum (square column) and by growth in the absence of the agonist in serum-free medium (open column).

Results

Figure 4:
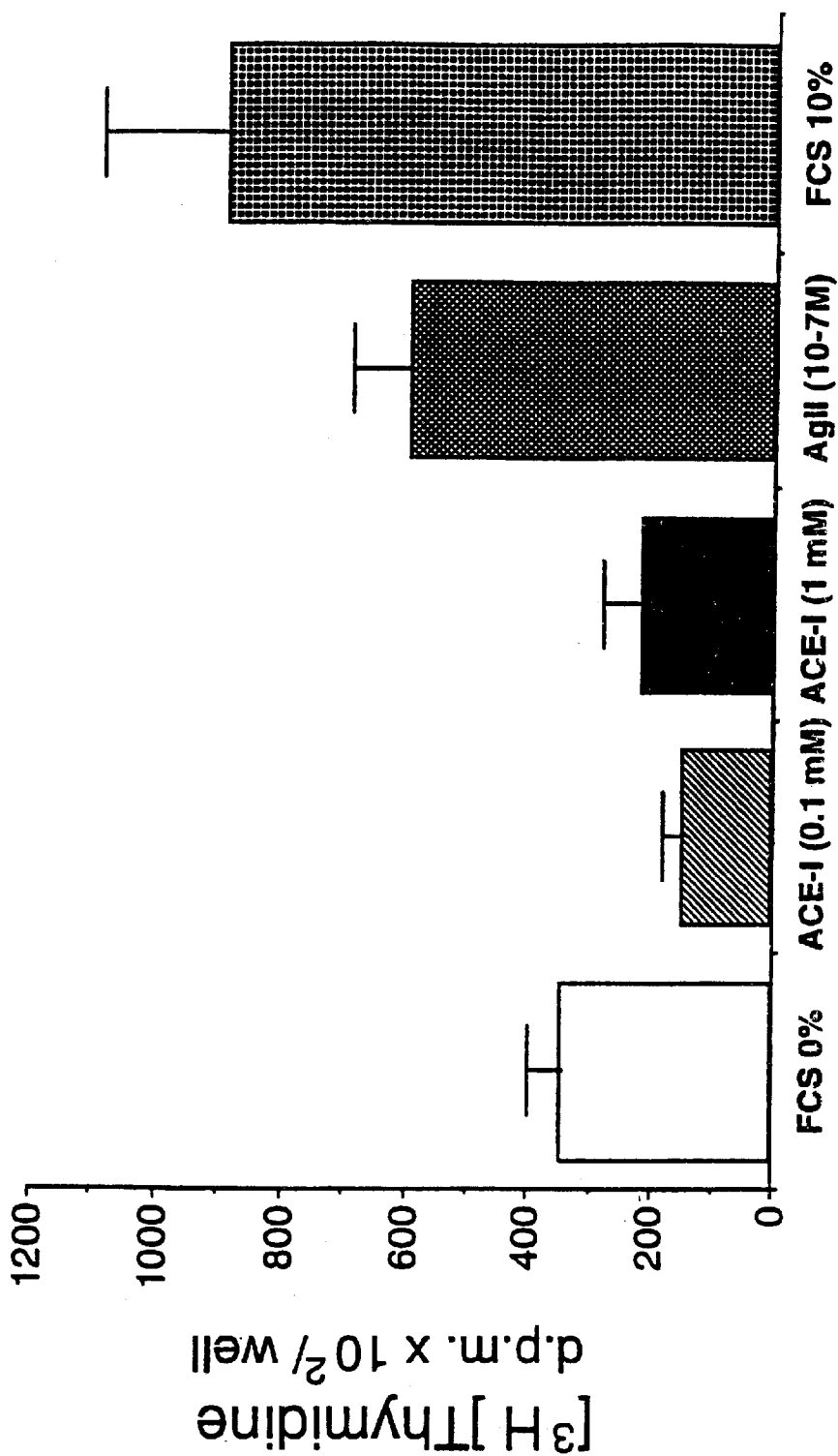
FIG. 4: Effect of an ACE inhibitor on cell proliferation.

As shown in FIG. 4, DNA synthesis was reduced by almost 50% of control (open column—0% FCS) in the presence of ACE inhibitor. This suggests that myometrial cells have the capacity to generate endogenous angiotensin II which promotes myometrial cell growth. Use of ACE inhibitors will reduce the ability of these cells to proliferate.

In another series of experiments, using the procedures described above in relation to FIGS. 3A and 3B, the results as shown in FIG. 4B were obtained. As FIG. 5 shows, angiotensin II-mediated cell proliferation is significantly inhibited when the cells are incubated with 1.00 $\mu$M of DuP753 or PD123177 or/and DuP753 plus PD123177. This suggests that in myometrial cells, angiotensin II stimulates cells proliferation via $AT_1$ or $AT_2$ receptor subtype.

Method of Treatment and Drug Administration

EXAMPLE

Treatment with Angiotensin Converting Enzyme Inhibitor Ramipril.

Start patient on 2.5 mg once daily for one week. Increase dose to 5 mg once daily for 12 weeks then increase dose to 10 mg for a further 12 weeks. Monitor size of fibroid and continue at this dose until fibroids fibroid/uterus reduces in size by 50%. Reduce dose to 5 mg once daily for as long as required. Drug may be orally administered.

I claim:

1. A method of treating uterine fibroids in a patient afflicted therewith, comprising administering to said patient a pharmaceutical agent selected from the group consisting of an angiotensin converting enzyme inhibitor, an angiotensin II-receptor antagonist, a renin inhibitor, and an angiotensin II-receptor expression inhibitor.

2. A method of treating uterine fibroids as claimed in claim 1, wherein the ACE inhibitor is selected from the group consisting of Captopril, Enalapril, Benazepril, Ramipril, Lisinopril, Imidapril 6366A, N-[8-amino-1-(S)-carboxyoctyl]-L-alanyl-L-proline and Pimobendan.

3. A method of treating uterine fibroids as claimed in claim 1, wherein the angiotensin II receptor antagonist is selected from the group consisting of Saralasin, Losartan, PD 123177, CGP 42112A, BIBS 39, BIBS 222, Sar-Ile-Ang II, Sar-Thr-Ang II, Sar-Ala-Ang II, Sar-Val-Ala-Ang II and Sar-O-Me-Tyr-Ang II.

4. A method of treating uterine fibroids as claimed in claim 1, wherein the renin inhibitor is selected from the group consisting of Remikiren, [N-(pyridyl-3 -propionyl)-phenylalanyl-histidyl-(3S,4S)-ACHPA-isoleucylamino]-2-methyl-2-dihydroxy-1-,3-propane, C1-992, and non-peptide renin inhibitors containing 2-(((3-phenylpropyl)phosphoryl) oxy) alkanoic acid moieties as $P_2$–$P_3$ replacements.

5. A method of treating uterine fibroids as claimed in claim 1, comprising the concomitant or sequential administration of a gonadotropin-releasing hormone agonist.

6. A method of treating uterine fibroids as claimed in claim 5, wherein the gonadotropin-releasing hormone agonist is selected from the group consisting of Buserelin and Goserelin.

* * * * *